United States Patent
Leal et al.

(10) Patent No.: US 12,264,123 B2
(45) Date of Patent: *Apr. 1, 2025

(54) METHOD OF PRODUCING A FUEL ADDITIVE

(71) Applicants: SABIC Global Technologies B.V., Bergen op Zoom (NL); Saudi Arabian Oil Company, Dhahran (SA)

(72) Inventors: Guillermo Leal, Riyadh (SA); Naif Mohammed Al-Naddah Al-Otaibi, Riyadh (SA); Kareemuddin Mahaboob Shaik, Dhahran (SA); Mohammed Bismillah Ansari, Riyadh (SA); Vijay Dinkar Bodas, Riyadh (SA)

(73) Assignees: SABIC GLOBAL TECHNOLOGIES B.V., Bergen op Zoom (NL); SAUDI ARABIAN OIL COMPANY, Dhahran (SA)

( * ) Notice: Subject to any disclaimer, the term of this patent is extended or adjusted under 35 U.S.C. 154(b) by 719 days.

This patent is subject to a terminal disclaimer.

(21) Appl. No.: 17/436,753

(22) PCT Filed: Mar. 5, 2020

(86) PCT No.: PCT/IB2020/051908
§ 371 (c)(1),
(2) Date: Sep. 7, 2021

(87) PCT Pub. No.: WO2020/183302
PCT Pub. Date: Sep. 17, 2020

(65) Prior Publication Data
US 2022/0185750 A1 Jun. 16, 2022

Related U.S. Application Data

(60) Provisional application No. 62/815,512, filed on Mar. 8, 2019.

(51) Int. Cl.
*C07C 29/04* (2006.01)
*B01D 3/00* (2006.01)
(Continued)

(52) U.S. Cl.
CPC .............. *C07C 29/04* (2013.01); *B01D 3/009* (2013.01); *C07C 4/06* (2013.01); *C07C 5/03* (2013.01);
(Continued)

(58) Field of Classification Search
CPC ..................................................... C07C 29/04
See application file for complete search history.

(56) References Cited

U.S. PATENT DOCUMENTS 3,061,654 A  10/1962  Gensheimer et al.
3,797,690 A   3/1974  Taylor et al.
(Continued)

FOREIGN PATENT DOCUMENTS

CA   2018524 A1  12/1990
CN   1044804 C    8/1999
(Continued)

OTHER PUBLICATIONS

Fuel Additives Selection Guide: Types, Features, Applications, Engineering 360, 4 pages, obtained May 11, 2022, http://www.globalspec.com/learnmore/materials_chemicals_adhesives/industrial_oils_fluids/fuel_oil_fluid_additives (Year: 2022).
(Continued)

*Primary Examiner* — Medhanit W Bahta
(74) *Attorney, Agent, or Firm* — CANTOR COLBURN LLP

(57) ABSTRACT

A method of producing a fuel additive includes passing a feed stream comprising $C_4$ hydrocarbons through a first hydrogenation unit producing a first process stream; passing the first process stream through a distillation unit; withdraw-
(Continued)

ing a 2-butene stream from the distillation unit: passing the 2-butene stream through a second hydrogenation unit producing a 1-butene stream; passing at least a portion of the 1-butene stream through a separation unit; and passing the 1-butene stream through a hydration unit producing the fuel additive.

20 Claims, 2 Drawing Sheets

(51) Int. Cl.
| | |
|---|---|
| C07C 4/06 | (2006.01) |
| C07C 5/03 | (2006.01) |
| C07C 5/05 | (2006.01) |
| C07C 7/00 | (2006.01) |
| C07C 7/04 | (2006.01) |
| C10L 1/02 | (2006.01) |
| C10L 1/182 | (2006.01) |

(52) U.S. Cl.
CPC ............. *C07C 5/05* (2013.01); *C07C 7/005* (2013.01); *C07C 7/04* (2013.01); *C10L 1/02* (2013.01); *C10L 1/1824* (2013.01)

(56) References Cited

U.S. PATENT DOCUMENTS

| | | |
|---|---|---|
| 3,849,082 A | 11/1974 | Kozlowski et al. |
| 3,912,463 A | 10/1975 | Kozlowski et al. |
| 4,267,397 A | 5/1981 | Schmidt et al. |
| 4,324,936 A | 4/1982 | Mikulicz |
| 4,334,890 A | 6/1982 | Kochar et al. |
| 4,336,046 A | 6/1982 | Schorre et al. |
| 4,356,339 A | 10/1982 | Imaizumi et al. |
| 4,408,085 A | 10/1983 | Gottlieb et al. |
| 4,423,251 A | 12/1983 | Pujado et al. |
| 4,436,946 A | 3/1984 | Smitny |
| 4,455,445 A | 6/1984 | Neuzil et al. |
| 4,499,313 A | 2/1985 | Okumura et al. |
| 4,540,831 A | 9/1985 | Briggs |
| 4,754,078 A | 6/1988 | Vora et al. |
| 4,773,968 A | 9/1988 | O'Connell et al. |
| 4,783,555 A | 11/1988 | Atkins |
| 4,797,133 A | 1/1989 | Pujado |
| 4,927,977 A | 5/1990 | Child et al. |
| 5,227,553 A | 7/1993 | Polanek et al. |
| 5,254,748 A | 10/1993 | Hensley et al. |
| 5,382,707 A | 1/1995 | Rubin et al. |
| 5,523,502 A | 6/1996 | Rubin |
| 5,563,299 A | 10/1996 | Paludetto et al. |
| 5,628,880 A | 5/1997 | Hearn et al. |
| 5,672,795 A | 9/1997 | Vora et al. |
| 5,864,052 A | 1/1999 | Nierlich et al. |
| 5,877,365 A | 3/1999 | Chodorge et al. |
| 5,898,091 A | 4/1999 | Chodorge et al. |
| 5,955,640 A | 9/1999 | Paludetto et al. |
| 6,580,009 B2 | 6/2003 | Schwab et al. |
| 7,227,047 B2 | 6/2007 | Risch et al. |
| 7,459,593 B1 | 12/2008 | Krupa et al. |
| 7,462,277 B2 | 12/2008 | Adrian et al. |
| 7,473,812 B2 | 1/2009 | Peters et al. |
| 7,485,761 B2 | 2/2009 | Schindler et al. |
| 8,124,572 B2 | 2/2012 | Miller |
| 8,395,007 B2 | 3/2013 | Wright et al. |
| 8,999,013 B2 | 4/2015 | Xu et al. |
| 9,187,388 B2 | 11/2015 | Arjah et al. |
| 9,611,192 B2 | 4/2017 | Digiulio |
| 10,774,020 B2 | 9/2020 | Di Girolamo et al. |
| 2002/0169346 A1 | 11/2002 | Commereuc et al. |
| 2003/0158429 A1 | 8/2003 | Albiez et al. |
| 2004/0171891 A1 | 9/2004 | Scholz et al. |
| 2005/0107628 A1 | 5/2005 | Roper et al. |
| 2005/0288534 A1 | 12/2005 | Fernandez et al. |
| 2007/0055088 A1* | 3/2007 | Schindler ............... C07C 5/333 585/702 |
| 2007/0149839 A1 | 6/2007 | Rix et al. |
| 2007/0265483 A1 | 11/2007 | Himelfarb |
| 2008/0146858 A1 | 6/2008 | Elomari et al. |
| 2008/0312481 A1 | 12/2008 | Leyshon |
| 2009/0193710 A1 | 8/2009 | Xiong et al. |
| 2011/0040133 A1 | 2/2011 | Vermeiren et al. |
| 2011/0230632 A1 | 9/2011 | Abhari |
| 2012/0117862 A1 | 5/2012 | Xu |
| 2012/0283492 A1 | 11/2012 | Dalemat et al. |
| 2013/0072732 A1 | 3/2013 | Breuil et al. |
| 2013/0104449 A1 | 5/2013 | Xu et al. |
| 2013/0172627 A1 | 7/2013 | Chewter et al. |
| 2013/0331620 A1 | 12/2013 | Abhari |
| 2014/0039226 A1 | 2/2014 | Xu et al. |
| 2014/0142350 A1 | 5/2014 | Weiner et al. |
| 2015/0225320 A1* | 8/2015 | Shaik ................... C07C 29/04 44/452 |
| 2015/0322181 A1 | 11/2015 | Kim et al. |
| 2016/0326079 A1 | 11/2016 | Lee et al. |
| 2017/0073289 A1 | 3/2017 | Leal et al. |
| 2017/0198231 A1 | 7/2017 | Xu et al. |
| 2017/0253540 A1 | 9/2017 | Hofel et al. |
| 2020/0157450 A1 | 5/2020 | Leal et al. |
| 2021/0002185 A1 | 1/2021 | Leal et al. |
| 2021/0024837 A1 | 1/2021 | Leal et al. |
| 2021/0024843 A1 | 1/2021 | Leal et al. |
| 2021/0155862 A1 | 5/2021 | Leal et al. |
| 2021/0171848 A1 | 6/2021 | Leal et al. |
| 2021/0214290 A1 | 7/2021 | Ansari et al. |
| 2021/0246088 A1 | 8/2021 | Leal et al. |

FOREIGN PATENT DOCUMENTS

| | | |
|---|---|---|
| CN | 1506344 A | 6/2004 |
| CN | 1736589 A | 2/2006 |
| CN | 101279879 A | 10/2008 |
| CN | 101289368 A | 10/2008 |
| CN | 102070391 A | 5/2011 |
| CN | 105585411 A | 5/2016 |
| CN | 106608791 A | 5/2017 |
| CN | 102372573 A | 3/2021 |
| EP | 0063813 B1 | 11/1982 |
| EP | 0102840 B1 | 3/1984 |
| EP | 0253679 | 1/1988 |
| EP | 0605822 A1 | 7/1994 |
| GB | 1374368 | 11/1974 |
| JP | S5920232 A | 2/1984 |
| JP | 2010111596 A | 5/2010 |
| RU | 2470905 C1 | 12/2012 |
| WO | 9011268 | 10/1990 |
| WO | 9732838 A1 | 9/1997 |
| WO | 0043336 A1 | 7/2000 |
| WO | 0146095 A1 | 6/2001 |
| WO | 2006113191 A2 | 10/2006 |
| WO | 2007024733 A2 | 3/2007 |
| WO | 2012095744 A2 | 7/2012 |
| WO | 2013104692 A1 | 7/2013 |
| WO | 2014153570 A2 | 9/2014 |
| WO | 2014160825 A1 | 10/2014 |
| WO | 2015089005 A1 | 6/2015 |
| WO | 2015123026 A1 | 8/2015 |
| WO | 2019207477 A1 | 10/2019 |

OTHER PUBLICATIONS

"Organic Chemistry"; Edited by Compilation Group of Chemistry Textbooks for Vocational and Technical Colleges; Higher Education Press; 2000; p. 66.

Ma Shichang et al.; "Dictionary of Chemical Substances"; Shaanxi Science and Technology Institute; 1999; p. 101.

Hua et al.; "Molecular Sieve-Catalyzed Mixed C Hydration"; Petrochemical Technology, vol. 34 Supplement; 2005; pp. 156-158.

Tianpu; "C3 and C4 Hydration Technology"; Qilu Petrochemical Technology, vol. 29, No. 3; 2001; pp. 218-223.

(56) References Cited

OTHER PUBLICATIONS

Zhiping et al.; "Discussion on Production Process Route of 1-Butene Products"; Chemical Industry and Engineering; 2003; pp. 178-184.
Bender et al.; "Selective Hydrogenation in Steam Cracking"; 21st Annual Saudi-Japan Symposium; Catalysts in Petroleum Refining & Petrochemicals; King Fahd University of Petroleum & Minerals; 2011; Abstract only; pp. 1-3.
Bodas et al.; U.S. Appl. No. 17/292,261; entitled "Process and System for Producing Ethylene and at Least One of Butanol and an Alkyl Tert-Butyl Ether"; filed with USPTO on May 7, 2021.
Brockwell et al.; "Synthesize ethers"; Hydrocarbon Processing, vol. 70, No. 9; 1991; pp. 133-141.
International Search Report for International Application No. PCT/IB2019/052177; International Filing Date Mar. 18, 2019; Date of Mailing Jun. 26, 2019; 3 pages.
International Search Report for International Application No. PCT/IB2019/052178; International Filing Date Mar. 18, 2019; Date of Mailing Jun. 26, 2019; 6 pages.
International Search Report for International Application No. PCT/IB2019/053697; International Filing Date May 6, 2019; Date of Mailing Aug. 28, 2019; 11 pages.
International Search Report for International Application No. PCT/IB2019/057784; International Filing Date Sep. 16, 2019; Date of Mailing Jan. 7, 2020; 5 pages.
International Search Report for International Application No. PCT/IB2019/059984; International Filing Date Nov. 20, 2019; Date of Mailing Feb. 21, 2020; 5 pages.
International Search Report for International Application No. PCT/IB2020/051908; International Filing Date Mar. 5, 2020; Date of Mailing May 29, 2020; 6 pages.
International Search Report for International Application No. PCT/US2019/026985; International Filing Date Apr. 11, 2019; Date of Mailing May 27, 2019; 6 pages.
International Search Report for International Application No. PCT/US2019/028092; International Filing Date Apr. 18, 2019; Date of Mailing Jun. 26, 2019; 6 pages.
International Search Report for International Application No. PCT/US2019/028099; International Filing Date Apr. 18, 2019; Date of Mailing Jun. 26, 2019; 6 pages.
International Search Report; International Application No. PCT/IB2018/055647; International Filing Date: Jul. 27, 2018; Date of Mailing: Oct. 30, 2018; 6 pages.
Izquierdo et al.; "Equilibrium Constants for Methyl tert-Butyl Ether Liquid-Phas Synthesis"; J. Chem. Eng. Data, vol. 37; 1992; pp. 339-343.
Kalamaras et al.; "SuperButol—a novel high-octane gasoline blending component"; Fuel, vol. 195; 2017; pp. 165-173.
Streich et al.; "Secure the Best Benefits from C4 Hydrocarbon Processing—Part 1: Separation Sequences"; Hydrocarbon Processing: Process Engineering and Optimization; 2016; 6 pages.
Written Opinion for International Application No. PCT/IB2019/052177; International Filing Date Mar. 18, 2019; Date of Mailing Jun. 26, 2019; 9 pages.
Written Opinion for International Application No. PCT/IB2019/052178; International Filing Date Mar. 18, 2019; Date of Mailing Jun. 26, 2019; 9 pages.
Written Opinion for International Application No. PCT/IB2019/053697; International Filing Date May 6, 2019; Date of Mailing Aug. 28, 2019; 9 pages.
Written Opinion for International Application No. PCT/IB2019/057784; International Filing Date Sep. 16, 2019; Date of Mailing Jan. 7, 2020; 7 pages.
Written Opinion for International Application No. PCT/IB2019/059984; International Filing Date Nov. 20, 2019; Date of Mailing Feb. 21, 2020; 8 pages.
Written Opinion for International Application No. PCT/IB2020/051908; International Filing Date Mar. 5, 2020; Date of Mailing May 29, 2020; 9 pages.
Written Opinion for International Application No. PCT/US2019/026985; International Filing Date Apr. 11, 2019; Date of Mailing May 27, 2019; 7 pages.
Written Opinion for International Application No. PCT/US2019/028092; International Filing Date Apr. 18, 2019; Date of Mailing Jun. 26, 2019; 9 pages.
Written Opinion for International Application No. PCT/US2019/028099; International Filing Date Apr. 18, 2019; Date of Mailing Jun. 26, 2019; 13 pages.
Written Opinion; International Application No. PCT/IB2018/055647; International Filing Date: Jul. 27, 2018; Date of Mailing: Oct. 30, 2018; 11 pages.

* cited by examiner

METHOD OF PRODUCING A FUEL ADDITIVE

CROSS REFERENCE TO RELATED APPLICATIONS

This application is a National Stage application of PCT/IB2020/051908, filed Mar. 5, 2020, which claims the benefit of U.S. Provisional Application No. 62/815,512, filed Mar. 8, 2019, both of which are incorporated by reference in their entireties herein.

BACKGROUND

Commercial gasoline, which is fuel for internal combustion engines, is a refined petroleum product that is typically a mixture of hydrocarbons (base gasoline), additives, and blending agents. Additives and blending agents, for example octane boosters, are added to the base gasoline to enhance the performance and the stability of gasoline.

When used in high compression internal combustion engines, gasoline has the tendency to "knock." Knocking occurs when combustion of the air/fuel mixture in the cylinder does not start off correctly in response to ignition because one or more pockets of air/fuel mixture pre-ignite outside the envelope of the normal combustion front. Anti-knocking agents, also known as octane boosters, reduce the engine knocking phenomenon, and increase the octane rating of the gasoline.

Hydrocarbon cracking processes are important conversion processes used in petroleum refineries. For example, fluid catalytic cracking ("FCC") is widely used to convert the high-boiling, high-molecular weight hydrocarbon fractions of petroleum crude oils to more valuable gasoline, olefinic gases, and other products. Thermal cracking of naphtha and gas oil is also widely used in the petrochemical industry to produce a variety of olefins and aromatics. For example, hydrocarbon feed stocks can be mixed with steam and subjected to elevated temperatures (e.g., 700-900° C.) in a steam cracker furnace wherein the feed stock components are cracked into various fractions. The effluent of the steam cracker can contain a gaseous mixture of hydrocarbons, for example, saturated and unsaturated olefins and aromatics (e.g., $C_1$-$C_{35}$ hydrocarbons). The effluent can then be separated into individual olefins (for example, ethylene, propylene, and CA hydrocarbons) and pyrolysis gasoline. Recycle streams of crude hydrocarbons are often formed as byproducts during these cracking processes.

The presence of isobutylene, butadiene, 1-butene, 2-butene, and other components within the crude hydrocarbon streams can allow for the formation of valuable alcohols and fuel additives. However, the conversion of crude hydrocarbon streams to fuel additive products can often be inefficient and costly. Furthermore, the final product specifications for such alcohols can be undesirable and can fail to meet market quality requirements. For example, alcohol products can have high levels of impurities, high Reid vapor pressures (e.g., greater than 10 kilopascals, greater than 12 kilopascals, greater than 13 kilopascals, greater than 14 kilopascals), and low octane numbers (e.g., 82 Research Octane Number ("RON")), all of which correlate with poor product quality. Any improvement in these specifications and/or the efficiency of the process can provide a more valuable fuel additive product.

Thus, there is a need for an efficient method of producing fuel additives that can make use of crude hydrocarbon streams and produce final products with low impurities and high performance specifications.

SUMMARY

Disclosed, in various embodiments, are methods of producing fuel additives.

A method of producing a fuel additive includes: passing a feed stream comprising $C_4$ hydrocarbons through a first hydrogenation unit producing a first process stream; passing the first process stream through a distillation unit; withdrawing a 2-butene stream from the distillation unit; passing the 2-butene stream through a second hydrogenation unit producing a 1-butene stream; passing at least a portion of the 1-butene stream through a separation unit; and passing the 1-butene stream through a hydration unit producing the fuel additive.

A method of producing a fuel additive includes: passing a feed stream comprising $C_4$ hydrocarbons through a first hydrogenation unit producing a first process stream, wherein greater than or equal to 90% by weight of butadiene present in the feed stream, based on the total weight of the butadiene present in the feed stream, is converted to 1-butene and/or 2-butene within the first hydrogenation unit; passing the first process stream through a distillation unit and withdrawing a 2-butene stream from the distillation unit; passing the 2-butene stream through a second hydrogenation unit producing a 1-butene stream; recycling at least a portion of the 1-butene stream back to the distillation unit; passing at least a portion of the 1-butene stream through a separation unit and through a hydration unit; and withdrawing a fuel additive product from the hydration unit, wherein the fuel additive product comprises greater than or equal to 0.5% by weight trimethylpentane based on the total weight of the fuel additive product, and the total weight of the fuel additive product is 100% by weight.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
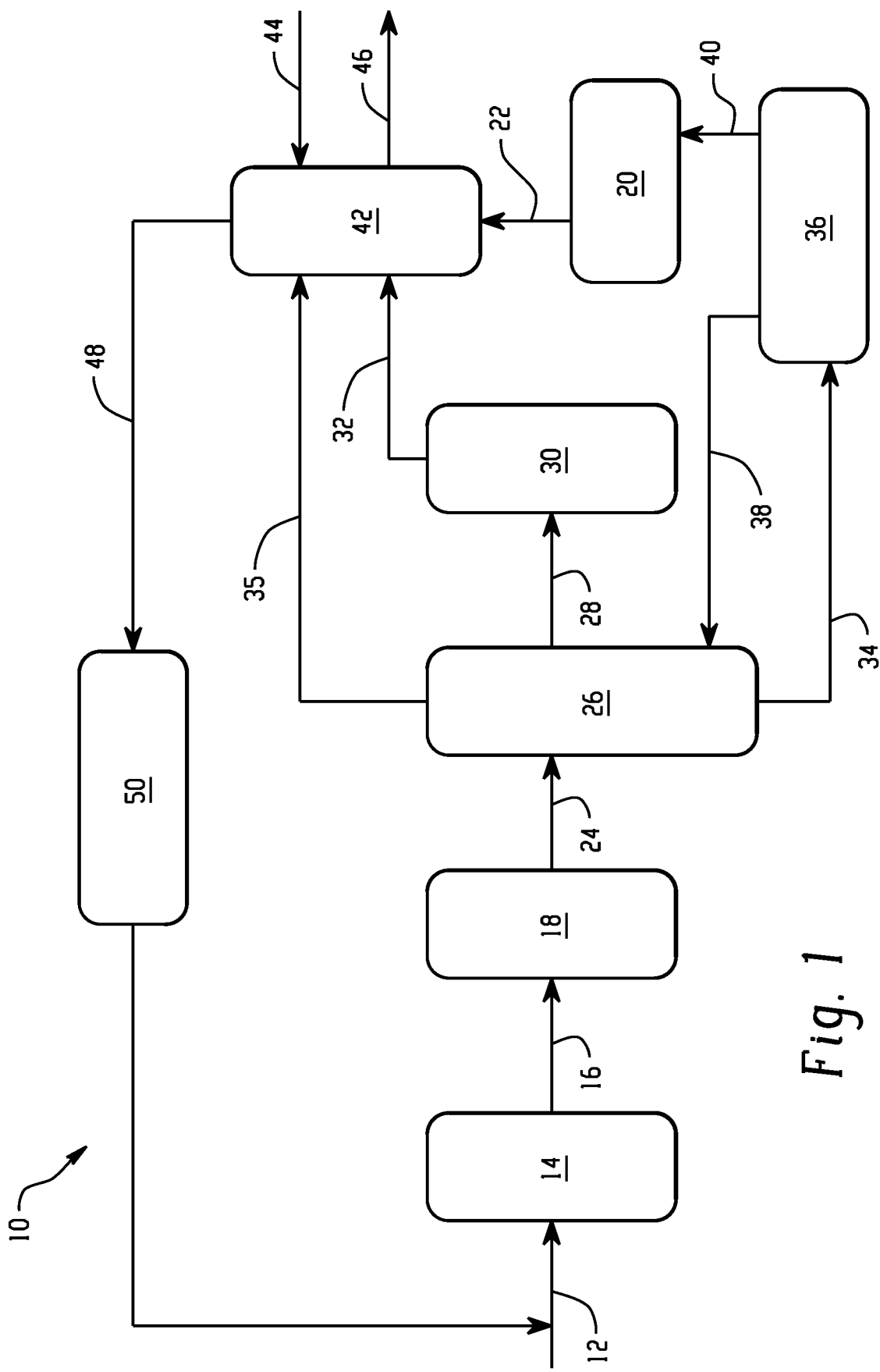
FIG. 1 is a schematic diagram representing a unit sequence for producing fuel additives.

Disclosed herein is an efficient method of producing fuel additives that can make use of crude hydrocarbon streams and produce final products with low impurities and high performance specifications. For example, the method disclosed herein can provide a unique sequence of unit operations that converts crude hydrocarbons into valuable fuel additives, such as alcohol fuel additives. This unique sequence can significantly improve the efficiency of the process, thereby reducing total capital costs. The final fuel additive products can have levels of 1-butanol, 2-butanol, tert-butyl alcohol, $C_4$-dimer, or a combination thereof. For example, the final fuel additive products can have levels of the $C_4$-dimer comprising trimethylpentane, di-isobutylene, 2,2,4 trimethylpentane, 2,3,3 trimethylpentane, or a combination thereof in an amount of 0.01% by weight to 50% by weight, based on the total weight of the fuel additive product (e.g., the total weight of the fuel additive product is 100% by weight), high octane numbers (e.g., greater than or equal to 85 RON, or greater than or equal to 87 RON), and low Reid vapor pressures of greater than or equal to 55 kilopascals. For example, the trimethylpentane in the fuel additive product can be present in an amount of 0.1 to 25% by weight, for example, 1 to 20% by weight, based on the total weight of the fuel additive product. Any one or all of these properties can correlate with high performance and high market value. The method disclosed herein can also produce secondary products along with the fuel additive product. For example, ethylene and propylene products can be produced along with the fuel additive, thus maximizing the efficiency and productivity of the process.

The method disclosed herein can provide a process for producing a fuel additive with a minimal number of components. For example, the inclusion of a hydrogenation unit, for example, a selective hydrogenation unit in the method can transform the butadiene components to 1-butene and 2-butene together with the utilization of isobutylene without the inclusion of a butadiene unit or a MTBE unit in the method. The method of making a fuel additive as disclosed can have increased efficiency by eliminating the inert n-butane and isobutane from the streams that are used as feedstocks for the hydration unit. Elimination of the use of these materials can increase efficiency by minimizing the amount of material to be recycled from the method. The method can produce fuel additives, for example, alcohol fuel additives, for example, $C_4$ fuel additives, from mixed crude hydrocarbon feedstocks, for example, $C_4$ hydrocarbons, from cracking units, such as steam cracking units with minimum capital expenditures and maximum production of the fuel additive with even further increased efficiency.

The method disclosed herein can provide a novel design for utilization and transformation of crude hydrocarbons from a cracking unit recycle stream as a feedstock to maximize production of the fuel additive. The method includes the use of selective hydrogenation units, distillation units, and hydration units for the maximum production of the fuel additive.

The method of making a fuel additive herein can include passing a feed stream of crude hydrocarbons through a first hydrogenation unit. For example, the crude hydrocarbons can include C hydrocarbons. The first hydrogenation unit can be a selective hydrogenation unit. This hydrogenation unit can convert the butadiene (BD) present in the feed stream to 1-butene and 2-butene, forming a first process stream. The first process stream can then be passed through a distillation unit, which can separate the first process stream into component hydrocarbons. The reduction of butadiene and the maximization of butenes in the feed stream can increase desirable product specifications of the fuel additive, for example, the octane number. A 2-butene stream can be withdrawn from the distillation unit and passed through a second hydrogenation unit. The second hydrogenation unit can convert 2-butene to 1-butene. A 1-butene stream can then be withdrawn from the second hydrogenation unit and passed through a separation unit. The separation unit can separate and isolate 1-butene. The 1-butene stream can then be passed through a hydration unit to produce the fuel additive, for example, a mixed alcohols fuel additive, for example, a $C_4$ alcohol fuel additive. Recycle streams from within the process can be used to produce ethylene and propylene as secondary products. Accordingly, the present process can maximize product quality for a fuel additive product while also producing additional secondary products in an efficient manner.

The method disclosed herein can include passing a raw material stream through an olefin production unit, for example, a hydrocarbon cracking unit, for example, a catalytic and/or steam cracking unit. The raw material stream can comprise hydrocarbons, for example, $C_4$ hydrocarbons. Additional hydrocarbons, for example, $C_2$ and $C_3$ hydrocarbons, can also be fed to the olefin production unit. A feed stream can then be withdrawn from the olefin production unit. The feed stream produced by the olefin production unit can comprise propylene, ethyl acetylene, vinyl acetylene, propadiene, 1, 3-butadiene, 1, 2-butadiene, isobutylene, cis-2-butene, trans-2-butene, 1-butene, isobutane, n-butane, propene, or a combination thereof. The total $C_4$ olefin content of the feed stream when withdrawn from a steam cracking unit can be greater than or equal to 90% by weight based on the total weight of the feed stream (e.g., the total weight of the feed stream is 100% by weight), and the feed stream can comprise greater than or equal to 15% by weight isobutylene, based on the total weight of the feed stream. The total $C_4$ olefin content of the feed stream when withdrawn from a fluid catalytic cracking unit can be greater than or equal to 35% by weight based on the total weight of the feed stream. The feed stream can comprise greater than or equal to 30% by weight isobutane and n-butane based on the total weight of the feed stream, for example, isobutylene in an amount of 10-25% by weight, olefins in an amount of 30-65% by weight, and saturated hydrocarbons in an amount of 30-65% by weight, based on the total weight of the feed stream.

The feed stream can then be passed through a first hydrogenation unit, for example, a selective hydrogenation unit. For example, the first hydrogenation unit can be a selective butadiene hydrogenation unit. The selective butadiene hydrogenation unit can selectively convert butadiene to 1-butene and 2-butene. The feed stream entering the first hydrogenation unit can comprise less than or equal to 50% by weight butadiene, for example, less than or equal to 30% by weight butadiene, for example, less than or equal to 42% by weight butadiene, based on the total weight of the feed stream (e.g., the total weight of the feed stream is 100% by weight). The first hydrogenation unit can convert butadiene present in the feed stream to 1-butene, cis-2-butene and trans-2-butene. The conversion rate from butadiene to 1-butene, cis-2-butene and/or trans-2-butene can be greater than or equal to 85% by weight (e.g., greater than or equal to 85% by weight of butadiene present in the feed stream, based on the total weight of the butadiene present in feed stream, is converted to 1-butene, cis-2-butene and/or trans-2-butene), for example, greater than or equal to 90% by weight, for example, greater than or equal to 95% by weight. The first hydrogenation unit can also convert propylene, methyl acetylene, and propadiene present in the process stream to their corresponding alkanes or alkenes, as appropriate. Tertiary butyl catechol and/or hydrogen can be added to the feed stream prior to passing through the first hydrogenation unit.

The first hydrogenation unit can comprise multiple reactors in series, for example, the unit can comprise three reactor stages. The first two reactor stages can convert butadiene present in the feed stream to 1-butene and 2-butene. The first two reactor stages can comprise a selective hydrogenation catalyst. For example, the hydrogenation catalyst can comprise palladium with an aluminum base. The hydrogenation catalyst can comprise platinum, rhodium, palladium, ruthenium, cobalt, nickel, copper, or a combination thereof. The catalyst can be the same for the first two reactor stages. Hydrogen can be injected into the feed stream prior to passing through the first reactor stage.

Final hydrogenation reaction of di-olefins to a desired product of mono-olefin can be achieved in the third reactor. Carbon monoxide can be injected into the third reactor to attenuate the catalyst and minimize the isomerization reaction from 1-butene to 2-butene. During normal operations, the desired carbon monoxide injection rate can be 2 parts per million of the feed stream to the third reactor. The rate can be increased if too much 1-butene is being lost to 2-butene. A first process stream can then be withdrawn from the hydrogenation unit. Operation conditions for the selective hydrogenation unit are shown in Table 1. Temperature is reported in degrees Celsius and pressure in pounds per square inch gauge (psig) and kiloPascals (kPa).

TABLE 1

| Reactor | Temp ° C. | Pressure (psig) | Catalyst | Representative butadiene content at exit |
|---|---|---|---|---|
| 1st Reactor | 40-70 | 140-400 (965-2758 kPa) | Noble metal/Alumina | 7% by weight |
| 2nd Reactor | 50-60 | 140-400 (965-2758 kPa) | Noble metal/Alumina | 1% by weight |
| 3rd Reactor | 60-80 | 250-270 (1724-1862 kPa) | Noble metal/Alumina | <0.01% by weight |

The first process stream can then be passed through a distillation unit, for example, a kinetic distillation unit. An overhead pressure in the distillation unit can be 600 to 1000 kPa and a reflux temperature can be 35-50° C. This distillation unit can separate the first process stream into component hydrocarbons. For example, a 2-butene stream can be withdrawn from the distillation unit. A temperature within the distillation unit can be 25° C. to 100° C., for example, 45° C. to 70° C. A pressure within the distillation unit can be 500 kPa to 1500 kPa, for example, 750 kPa to 1200 kPa, for example, 785 kPa to 1175 kPa.

The 2-butene stream withdrawn from the distillation unit can be passed through a second hydrogenation unit. The 2-butene stream can comprise n-butane, 1-butene, and 2-butene. The second hydrogenation unit can convert 2-butene present in the 2-butene stream to 1-butene. Pressure in the second hydrogenation unit can be 500 to 1500 kPa and a reflux temperature can be 180-300° C. A portion of the 1-butene stream can then be withdrawn from the second hydrogenation unit and recycled back to the distillation unit. The 1-butene stream can comprise 1-butene and n-butane. A portion of the 1-butene stream can optionally be passed through a separation unit together with the isobutylene stream. A temperature within the distillation unit can be 25° C. to 100° C. for example, 45° C. to 70° C. A pressure within the distillation unit can be 500 kilopascals to 1500 kilopascals, for example, 750 kilopascals to 1200 kilopascals, for example, 785 kilopascals to 1175 kilopascals. The separation unit can separate and isolate 1-butene and isobutylene. A separated 1-butene stream and isobutylene stream can then be withdrawn from the separation unit and passed through a hydration unit.

The hydration unit can hydrate the isobutylene stream and a second stream (comprising butenes) to produce a fuel additive, for example, an alcohol fuel additive, for example, a mixed alcohols fuel additive, for example, a $C_4$ alcohol fuel additive. The 1-butene stream entering the hydration unit can comprise less than or equal to 5% by weight butadiene, for example, less than or equal to 3% by weight, for example, less than or equal to 1% by weight based on the total weight of the 1-butene stream (e.g., the total weight of the 1-butene stream is 100% by weight). The fuel additive product can be withdrawn from the hydration unit via a product stream. Water can be fed to the hydration unit via a water stream. The hydration unit can comprise an oscillating baffle reactor, a fixed bed reactor, a membrane integrated reactor, isothermal multi-tubular reactor, or a combination thereof. The hydration unit can convert butene present in the process stream to butanol. For example, 17-99% by weight of the butene present in the 1-butene stream, based on the total weight of the butene present in the 1-butene stream, can be converted to butanol within the hydration unit. The 1-butene stream can be contacted with water and a catalyst within the hydration unit. For example, the catalyst can comprise phosphoric acid, hypophosphorous acid, sulfonic ion-exchange resin, super acid resins niobium oxide, or a combination thereof. Water and butene can be present within the hydration unit in a molar ratio of 1.0-15.0 mole of water to 1 mole of butene, for example, 10 mole of water to 1 mole of butene. A temperature within the hydration unit can be 30° C. to 250° C., for example, 100° C. to 200° C. A pressure within the hydration unit can be 500 kPa to 20,000 kPa, for example, 5000 kPa to 10,000 kPa, for example, 7500 kPa.

The fuel additive product can comprise 1-butanol, 2-butanol, tert-butyl alcohol, $C_4$-dimer, or a combination thereof. For example, the $C_4$-dimer can comprise di-isobutylene, 2,2,4 trimethylpentane, 2,3,3 trimethylpentane, or a combination thereof. The fuel additive product can comprise greater than or equal to 5% by weight trimethylpentane, for example, greater than or equal to 10% by weight, for example, greater than or equal to 15% by weight, for example greater than or equal to 20% by weight, based on the total weight of the fuel additive product (e.g., the total weight of the fuel additive product is 100% by weight). An octane number of the fuel additive product can be greater than or equal to 80 according to the Anti-Knock Index, for example, greater than or equal to 85, for example, greater than or equal to 90, for example, greater than or equal to 93, for example greater than or equal to 95.

The octane number is a standard measurement used to gauge the performance of an engine or fuel. The higher the octane number, the more compression the fuel is able to withstand before igniting. Fuels with higher octane ratings are generally used in high performance gasoline engines that need higher compression ratios. Fuels with lower octane numbers can be desirable for diesel engines because diesel engines do not compress the fuel, but rather compress only air and then inject fuel into the air which is heated by compression. Gasoline engines rely on ignition of air and fuel compressed together as a mixture, which is ignited at the end of the compression stroke using spark plugs. As a result, high compressibility of fuel is a consideration for gasoline engines.

The Anti-Knock Index is measured by adding the Research Octane Number ("RON") and the Motor Octane Number ("MON") and dividing by two, e.g., (RON+MON)/2. The Research Octane Number is determined by running the fuel in a test engine at a speed of 600 revolutions per minute with a variable compression ratio under controlled conditions, and comparing the results with those for mixtures of iso-octane and n-heptane. Motor Octane Number is determined by testing a similar test engine to that used in determining the Research Octane Number but at a speed of 900 revolutions per minute with a preheated fuel mixture, higher engine speed, and variable ignition timing. Depending on the composition, the Motor Octane Number can be about 8 to 12 octanes lower than the Research Octane Number. The Research Octane Number can be greater than or equal to 88, for example, greater than or equal to 91, for example, greater than or equal to 93, for example, greater than or equal to 95, for example, greater than or equal to 100. The Motor Octane Number can be greater than or equal to 82, for example, greater than or equal to 89, for example, greater than or equal to 90, for example, greater than or equal to 93. Higher octane ratings can give higher amounts of energy needed to initiate combustion. Fuels with higher octane ratings are less prone to auto-ignition and can withstand a greater rise in temperature during the compression stroke of an internal combustion engine without auto-igniting.

Reid vapor pressure is used to measure the volatility of gasoline defined as the absolute vapor pressure exerted by a liquid at 37.8° C. as determined by the test method ASTM D-323. Reid vapor pressure is measured in kilopascals and represents a relative pressure to atmospheric pressure since ASTM D-323 measures the gauge pressure of the sample in a non-evacuated chamber. High levels of vaporization are desired for winter starting and operation and lower levels are desirable in avoiding vapor lock during summer heat. Fuel generally cannot be pumped when vapor is present in the fuel line, and winter starting can be difficult when liquid gasoline in the combustion chambers has not vaporized. This means that the Reid vapor pressure is changed accordingly by oil producers seasonally to maintain gasoline engine reliability.

The Reid vapor pressure of the fuel additive product can be less than or equal to 55.16 kilopascals, for example, 5 kilopascals to 55 kilopascals, for example, 5 kilopascals to 40 kilopascals. The Reid vapor pressure can vary during winter and summer conditions such that the pressure can be at the higher end of the values during the winter and at the lower end of the values during the summer.

A recycle stream, e.g., a hydrocarbon recycle stream, can be withdrawn from the hydration unit as a purge stream and recycled to the raw material stream and/or the olefin production unit, such as a steam cracker unit. The recycle stream can comprise butene, isobutane, n-butane, isobutylene, or a combination thereof. The recycle stream can optionally be passed through a recycle hydrogenation unit prior to returning to the raw material stream. The recycle hydrogenation unit can convert the 1-butene and 2-butene present in the recycle stream to n-butane and isobutane. For example, greater than or equal to 90% by weight of butene present in the hydrocarbon recycle stream, based on the total weight of the butene present in the hydrocarbon recycle stream, can be converted to butane within the recycle hydrogenation unit (e.g., the total weight of the butene present in the hydrocarbon recycle stream is 100% by weight). The hydrocarbon recycle stream can also be used to produce secondary products such as ethylene and propylene via a hydrocarbon cracking unit.

Additional recycle streams can be withdrawn from within the process. For example, an iso-stream comprising isobutane and/or isobutylene can be withdrawn from the distillation unit. The iso-stream can comprise greater than or equal to 90% by weight isobutane and/or isobutylene, based on the total weight of the iso-stream (e.g., the total weight of the iso-stream is 100% by weight). A butane stream comprising n-butane and/or isobutane can be withdrawn from the distillation unit and/or the separation unit. The iso-stream and/or the butane stream can be recycled back to the raw material stream and/or the cracking unit (in a manner similar to the hydrocarbon recycle stream). The iso-stream and/or the butane stream can be fed directly to the hydration unit as additional feedstock for production of the fuel additive product. The iso-stream and/or the butane stream can also be used to produce secondary products such as ethylene and propylene via a hydrocarbon cracking unit.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Referring now to FIG. 1, this simplified schematic diagram represents a unit sequence 10 used in a method for producing fuel additives. The sequence 10 can include passing a raw material stream 12 comprising hydrocarbons through a hydrocarbon cracking unit 14. For example, the hydrocarbon cracking unit 14 can be a steam cracking and/or catalytic cracking unit.

A feed stream 16 can then be withdrawn from the cracking unit 14. The feed stream 16 can comprise crude hydrocarbons, for example, $C_4$ hydrocarbons. The feed stream 16 can then be passed through a first hydrogenation unit 18, for example, a selective hydrogenation unit. The first hydrogenation unit 18 can be a selective butadiene hydrogenation unit and can comprise multiple reactors in series. This hydrogenation unit 18 can convert butadiene present in the feed stream 16 to 1-butene and 2-butene.

A first process stream 24 can then be withdrawn from the first hydrogenation unit 18 and passed through a distillation unit 26 (e.g., kinetic distillation column 26). This distillation unit 26 can separate the first process stream 24 into component hydrocarbons. A 2-butene stream 34 can be withdrawn from the distillation unit 26 and passed through a second hydrogenation unit 36.

The second hydrogenation unit 36 can convert 2-butene present in the stream 34 to 1-butene. A 1-butene stream 38 can then be withdrawn from the second hydrogenation unit 36 and recycled back to the distillation unit 26. A portion of the 1-butene stream can be passed through a separation unit 20 via stream 40. The separation unit 20 can separate and isolate 1-butene.

A separated 1-butene stream 22 can then be withdrawn from the separation unit 20 and passed through a hydration unit 42. The hydration unit 42 can hydrate the 1-butene stream 22 to produce a fuel additive 46, for example, an alcohol fuel additive. The fuel additive 46 can be withdrawn from the hydration unit 42. Water can be fed to the hydration unit 42 via stream 44. It is noted that the hydration unit can take the form of an oscillating baffle reactor, a fixed bed reactor, a fluidized bed reactor, a membrane integrated reactor, or combinations thereof.

A hydrocarbon recycle stream 48 can be withdrawn from the hydration unit 42 and recycled back to the raw material stream 12 and/or the cracking unit 14. The recycle stream 48 can be passed through an additional (e.g., a third) hydrogenation unit 50 prior to returning to the raw material stream 12. An iso-stream 28 comprising isobutane and/or isobutylene can also be withdrawn from the distillation unit 26. A butane stream 35 comprising n-butane and/or isobutane can further be withdrawn from the distillation unit 26.

The iso-stream 28 and/or the butane stream 35 can be recycled back to the raw material stream 12 and/or the cracking unit 14 (in a manner similar to the hydrocarbon recycle stream 48). The iso-stream 28 and/or the butane stream 35 can also be used to produce secondary products such as ethylene and propylene.

The following example is merely illustrative of the method of treating pyrolysis gasoline disclosed herein and is not intended to limit the scope hereof. Unless otherwise stated, the example was based upon simulations.

EXAMPLE

Example 1

Figure 2:
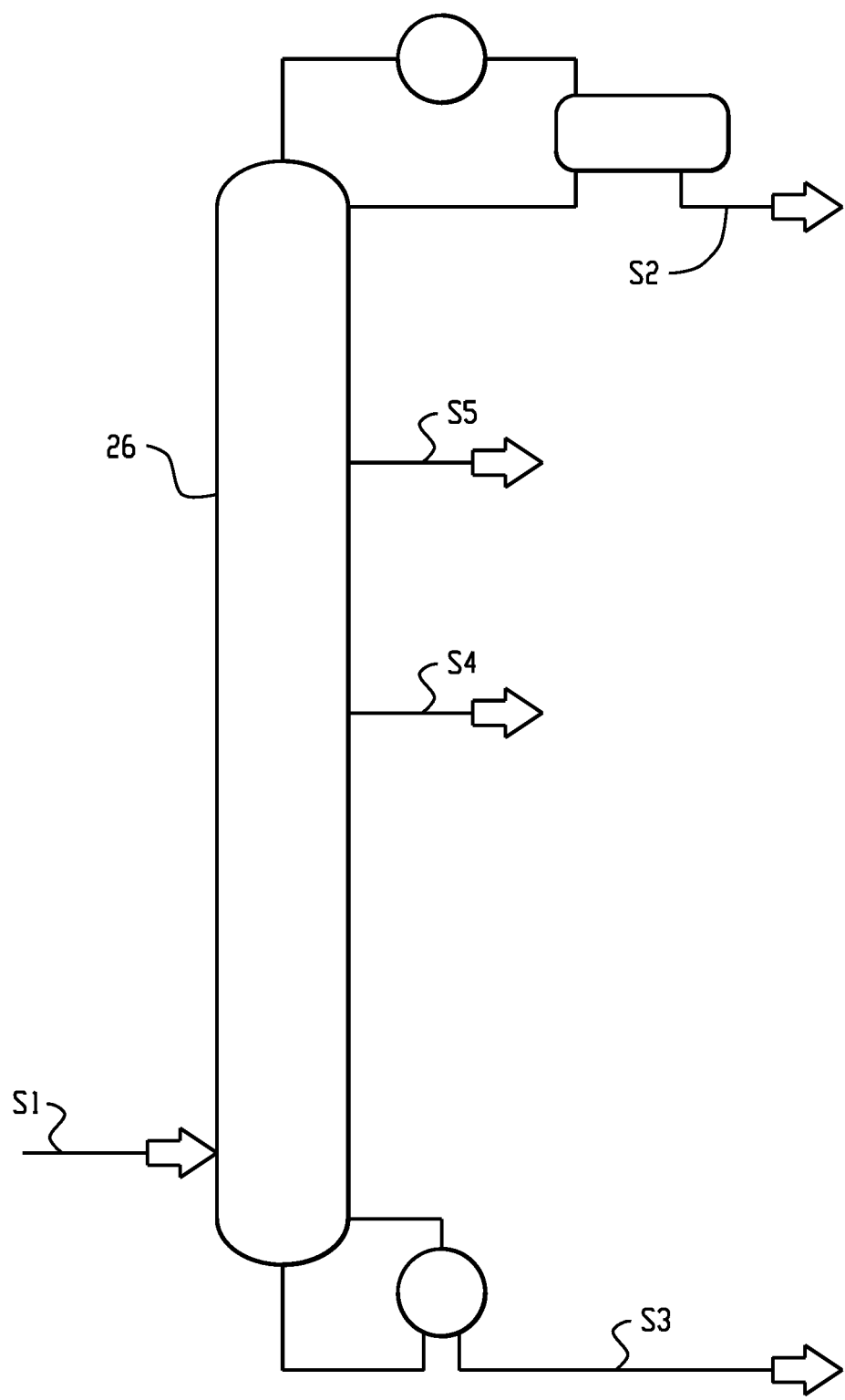
FIG. 2 is a schematic diagram representing the streams in Example 1.

Simulations were conducted using Aspen Plus and Pro/II 10.0 (chemical engineering computer software programs) for the distillation unit 26 of the present method. The results from the simulation are presented in Table 2. As shown in FIG. 2, Stream 1 (e.g., similar to first process stream 24 from FIG. 1) represents the stream entering the distillation unit 26 and Streams 2-5 represent product streams being withdrawn from the unit 26. This can be seen in FIG. 2, where Stream 1 (S1) is entering the distillation unit 26 and Streams 2-5 (S2, S3, S4, and S5) are being withdrawn from the distillation unit 26. Temperature for each Stream S1-S5 is given in degrees Celsius, pressure is given in kilograms per square centimeter ("$kg/cm^2$"), and flowrate is given in kilogram-moles per hour ("kg-mol/hr"). The fractional compositions of the Streams S1-S5 are also provided by mole % (mole % is based on the total moles of the respective Stream S1 to S5—e.g., the mole % of isobutane of Stream S1 is based on the total moles of Stream S1).

TABLE 2

Distillation Unit (Column Data

| | Stream | | | | |
|---|---|---|---|---|---|
| | 1 | 2 | 4 | 3 | 5 |
| Phase | Liquid | Liquid | Liquid | Liquid | Liquid |
| Temperature (° C.) | 46.000 | 56.139 | 60.391 | 68.796 | 59.992 |
| Pressure ($kg/cm^2$) | 12.000 | 8.000 | 8.001 | 8.002 | 8.000 |
| Flowrate (kg-mol/hr) | 1501.543 | 271.133 | 17.835 | 817.208 | 395.476 |
| Fraction Composition (mole %) | | | | | |
| isobutane | 0.149 | 0.774 | 0.000 | 0.000 | 0.034 |
| N-butane | 0.340 | 0.000 | 0.000 | 0.624 | 0.000 |
| 1-butene | 0.135 | 0.046 | 0.581 | 0.044 | 0.363 |
| Cis-2-butene | 0.089 | 0.000 | 0.000 | 0.163 | 0.000 |
| Trans-2-butene | 0.082 | 0.000 | 0.000 | 0.150 | 0.000 |
| Isobutylene | 0.198 | 0.180 | 0.419 | 0.004 | 0.603 |
| 2-methyl-1-butene | 0.008 | 0.000 | 0.000 | 0.015 | 0.000 |

Stream 2, Stream S4 and/or Stream S5 (e.g., similar to iso-stream 28 and/or butane stream 35 from FIG. 1) can be sent to the hydration unit 42, and Stream S3 (e.g., similar to 2-butene stream 34 from FIG. 1) is a stream that includes no or trace amounts of isobutylene (e.g., Stream 3 has 0.004 mole % isobutylene, as shown in Table 2 above), and can be sent to the second hydrogenation unit 36, as discussed above in conjunction with FIG. 1.

The methods disclosed herein include(s) at least the following aspects:

Aspect 1: A method of producing a fuel additive, comprising: passing a feed stream comprising $C_4$ hydrocarbons through a first hydrogenation unit producing a first process stream; passing the first process stream through a distillation unit; withdrawing a 2-butene stream from the distillation unit; passing the 2-butene stream through a second hydrogenation unit producing a 1-butene stream; passing at least a portion of the 1-butene stream through a separation unit; and passing the 1-butene stream through a hydration unit producing the fuel additive.

Aspect 2: The method of Aspect 1, wherein the feed stream comprises a product of a catalytic cracking process and/or an olefin production process.

Aspect 3: The method of any of the preceding aspects, wherein the feed stream comprises methyl acetylene, propylene, 1,3-butadiene, 1,2-butadiene, isobutylene, cis-2-butene, trans-2-butene, 1-butene, isobutane, n-butane, or a combination thereof.

Aspect 4: The method of any of the preceding aspects, wherein the distillation unit comprises a kinetic distillation column.

Aspect 5: The method of any of the preceding aspects, wherein greater than or equal to 85% by weight, preferably, greater than or equal to 90% by weight, more preferably, greater than or equal to 95% by weight of butadiene present in the feed stream, based on the total weight of the butadiene present in the feed stream, is converted to 1-butene and/or 2-butene within the first hydrogenation unit.

Aspect 6: The method of any of the preceding aspects, further comprising passing a water stream through the hydration unit.

Aspect 7: The method of any of the preceding aspects, further comprising adding tertiary butyl catechol and/or hydrogen to the feed stream prior to passing through the first hydrogenation unit.

Aspect 8: The method of any of the preceding aspects, further comprising withdrawing an iso-stream from the first distillation unit, wherein the iso-stream comprises isobutane and isobutylene.

Aspect 9: The method of Aspect 8, further comprising recycling the iso-stream back to the raw material stream.

Aspect 10: The method of Aspect 8, further comprising passing the iso-stream through a propylene and/or ethylene cracking unit.

Aspect 11: The method of Aspect 8, further comprising passing the iso-stream through the hydration unit.

Aspect 12: The method of any of the preceding aspects, further comprising recycling at least a portion of the 1-butene stream back to the distillation unit.

Aspect 13: The method of any of the preceding aspects, further comprising withdrawing a butane stream comprising n-butane and/or isobutane from the separation unit and passing the butane stream through a propylene and/or ethylene cracking unit.

Aspect 14: The method of any of the preceding aspects, wherein the hydration unit comprises an oscillating baffle reactor, a fixed bed reactor, a fluidized bed reactor, a membrane integrated reactor, or a combination thereof.

Aspect 15: The method of any of the preceding aspects, wherein greater than or equal to 0.1% by weight of butene present in the 1-butene stream, based on the total weight of the butene present in the 1-butene stream, is converted to butanol within the hydration unit. It is noted that the total weight of the butene present in the 1-butene stream is 100% by weight.

Aspect 16: The method of any of the preceding aspects, further comprising withdrawing a fuel additive product from the hydration unit, wherein the fuel additive product comprises 1-butanol, 2-butanol, tert-butyl alcohol, $C_4$ dimer, or a combination thereof, preferably, wherein the $C_4$ dimer comprises 1-butanol, di-isobutylene, 2.2.4 trimethylpentane, 2,3,3 trimethylpentane, or a combination thereof.

Aspect 17: The method of Aspect 16, wherein the fuel additive product comprises greater than or equal to 0.01% by weight and less than or equal to 20% by weight trimethylpentane based on the total weight of the fuel additive product, and the total weight of the fuel additive product is 100% by weight.

Aspect 18: The method of Aspect 16, wherein an octane number of the fuel additive product is greater than or equal to 85 in accordance with the Anti-Knock Index.

Aspect 19: The method of Aspect 16, wherein a Reid vapor pressure of the fuel additive product is less than or equal to 75 kilopascals, preferably, less than or equal to 65 kilopascals, preferably, less than or equal to 55.16 kilopascals.

Aspect 20: A method of producing a fuel additive, comprising: passing a feed stream comprising $C_4$ hydrocarbons through a first hydrogenation unit producing a first process stream, wherein greater than or equal to 90% by weight of butadiene present in the feed stream, based on the total weight of the butadiene present in the feed stream, is converted to 1-butene and/or 2-butene within the first hydrogenation unit; passing the first process stream through a distillation unit and withdrawing a 2-butene stream from the distillation unit; passing the 2-butene stream through a second hydrogenation unit producing a 1-butene stream; recycling at least a portion of the 1-butene stream back to the distillation unit; passing at least a portion of the 1-butene stream through a separation unit and through a hydration unit; and withdrawing a fuel additive product from the hydration unit, wherein the fuel additive product comprises greater than or equal to 0.5% by weight trimethylpentane based on the total weight of the fuel additive product, and the total weight of the fuel additive product is 100% by weight. It is noted that the total weight of the butadiene present in the feed stream is 100% by weight.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %." etc.). Disclosure of a narrower range or more specific group in addition to a broader range is not a disclaimer of the broader range or larger group. "Combination" is inclusive of blends, mixtures, alloys, reaction products, and the like. Furthermore, the terms "first." "second." and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like. In a list of alternatively useable species, "a combination thereof" means that the combination can include a combination of at least one element of the list with one or more like elements not named. Also, "at least one of" means that the list is inclusive of each element individually, as well as combinations of two or more elements of the list, and combinations of at least one element of the list with like elements not named.

As used herein, the term "$C_\#$ hydrocarbons" or "$C_\#$" wherein "#" is a positive integer, describes hydrocarbons having # carbon atoms. Accordingly, the term "$C_4$ hydrocarbons" describes hydrocarbons having 4 carbon atoms.

All test standards and methods, such as ASTM, AOCS, and ISO, are the most recent standard as of Mar. 8, 2019, unless specified otherwise.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of producing a fuel additive, comprising:
   passing a feed stream comprising $C_4$ hydrocarbons through a first hydrogenation unit producing a first process stream;

passing the first process stream through a distillation unit;
withdrawing a 2-butene stream from the distillation unit;
passing the 2-butene stream through a second hydrogenation unit producing a 1-butene stream;
passing at least a portion of the 1-butene stream produced in the second hydrogenation unit through a separation unit producing a separated 1-butene stream; and
passing the separated 1-butene stream produced in the separation unit through a hydration unit producing the fuel additive,
wherein
the distillation unit comprises a kinetic distillation column,
the method further comprises withdrawing an iso-stream from the distillation unit, passing a raw material stream comprising hydrocarbons through a hydrocarbon cracking unit, withdrawing the feed stream from the cracking unit, and recycling the iso-stream back to the raw material stream, wherein the iso-stream comprises isobutane and isobutylene, and wherein the iso-stream comprises greater than or equal to 90% by weight isobutane and/or isobutylene, based on the total weight of the iso-stream,
the method further comprises withdrawing an iso-stream from the distillation unit, and passing the iso-stream through a propylene and/or ethylene cracking unit, wherein the iso-stream comprises isobutane and isobutylene, and wherein the iso-stream comprises greater than or equal to 90% by weight isobutane and/or isobutylene, based on the total weight of the iso-stream, or
the method further comprises withdrawing a butane stream comprising n-butane and/or isobutane from the separation unit and passing the butane stream through a propylene and/or ethylene cracking unit.

2. The method of claim 1, wherein the feed stream comprises a product of a catalytic cracking process and/or an olefin production process.

3. The method of claim 1, wherein the feed stream comprises at least one of methyl acetylene, propylene, 1,3-butadiene, 1,2-butadiene, isobutylene, cis-2-butene, trans-2-butene, 1-butene, isobutane, or n-butane.

4. The method of claim 1, wherein the distillation unit comprises a kinetic distillation column.

5. The method of claim 1, wherein the feed stream comprises butadiene and greater than or equal to 85% by weight of the butadiene present in the feed stream, based on the total weight of the butadiene present in the feed stream, is converted to 1-butene and/or 2-butene within the first hydrogenation unit.

6. The method of claim 1, further comprising passing a water stream through the hydration unit.

7. The method of claim 1, further comprising adding tertiary butyl catechol and/or hydrogen to the feed stream prior to passing through the first hydrogenation unit.

8. The method of claim 1, further comprising withdrawing an iso-stream from the distillation unit, wherein the iso-stream comprises isobutane and isobutylene, and wherein the iso-stream comprises greater than or equal to 90% by weight isobutane and/or isobutylene, based on the total weight of the iso-stream.

9. The method of claim 8, further comprising passing a raw material stream comprising hydrocarbons through a hydrocarbon cracking unit, withdrawing the feed stream from the cracking unit, and recycling the iso-stream back to the raw material stream.

10. The method of claim 8, further comprising passing the iso-stream through a propylene and/or ethylene cracking unit.

11. The method of claim 8, further comprising passing the iso-stream through the hydration unit.

12. The method of claim 1, further comprising recycling at least a portion of the 1-butene stream back to the distillation unit.

13. The method of claim 1, further comprising withdrawing a butane stream comprising n-butane and/or isobutane from the separation unit and passing the butane stream through a propylene and/or ethylene cracking unit.

14. The method of claim 1, wherein the hydration unit comprises an oscillating baffle reactor, a fixed bed reactor, a fluidized bed reactor, a membrane integrated reactor, or a combination thereof.

15. The method of claim 1, wherein the 1-butene stream comprises butene and greater than or equal to 0.1% by weight of the butene present in the 1-butene stream, based on the total weight of the butene present in the 1-butene stream, is converted to butanol within the hydration unit.

16. The method of claim 1, further comprising withdrawing a fuel additive product from the hydration unit, wherein the fuel additive product comprises at least one of 1-butanol, 2-butanol, tert-butyl alcohol, or a $C_4$ dimer.

17. The method of claim 16, wherein the fuel additive product comprises greater than or equal to 0.01% by weight and less than or equal to 20% by weight trimethylpentane based on the total weight of the fuel additive product, and the total weight of the fuel additive product is 100% by weight.

18. The method of claim 16, wherein an octane number of the fuel additive product is greater than or equal to 85 in accordance with the Anti-Knock Index, and wherein a Reid vapor pressure of the fuel additive product is less than or equal to 75 kilopascals.

19. A method of producing a fuel additive, comprising:
passing a feed stream comprising $C_4$ hydrocarbons through a first hydrogenation unit producing a first process stream, wherein greater than or equal to 90% by weight of butadiene present in the feed stream, based on the total weight of the butadiene present in the feed stream, is converted to 1-butene and/or 2-butene within the first hydrogenation unit;
passing the first process stream through a distillation unit and withdrawing a 2-butene stream from the distillation unit;
passing the 2-butene stream through a second hydrogenation unit producing a 1-butene stream;
recycling at least a portion of the 1-butene stream back to the distillation unit;
passing at least a portion of the 1-butene stream through a separation unit and through a hydration unit; and
withdrawing a fuel additive product from the hydration unit, wherein the fuel additive product comprises greater than or equal to 0.5% by weight trimethylpentane based on the total weight of the fuel additive product, and the total weight of the fuel additive product is 100% by weight.

20. A method of producing a fuel additive, comprising:
passing a feed stream comprising $C_4$ hydrocarbons through a first hydrogenation unit producing a first process stream;
passing the first process stream through a distillation unit;
withdrawing a 2-butene stream from the distillation unit;
passing the 2-butene stream through a second hydrogenation unit producing a 1-butene stream;

passing at least a portion of the 1-butene stream through a separation unit; and passing the 1-butene stream through a hydration unit producing the fuel additive, wherein the distillation unit comprises a kinetic distillation column, the method further comprises passing a raw material stream comprising hydrocarbons through a hydrocarbon cracking unit, withdrawing the feed stream from the cracking unit, withdrawing an iso-stream from the distillation unit, wherein the iso-stream comprises isobutane and isobutylene, and recycling the iso-stream back to the raw material stream, the method further comprises withdrawing an iso-stream from the distillation unit, wherein the iso-stream comprises isobutane and isobutylene, and passing the iso-stream through a propylene and/or ethylene cracking unit, the method further comprises withdrawing a butane stream comprising n-butane and/or isobutane from the separation unit and passing the butane stream through a propylene and/or ethylene cracking unit, the method further comprises withdrawing a fuel additive product from the hydration unit, wherein the fuel additive product comprises at least one of 1-butanol, 2-butanol, tert-butyl alcohol, or a $C_4$ dimer and the fuel additive product comprises greater than or equal to 0.01% by weight and less than or equal to 20% by weight trimethylpentane based on the total weight of the fuel additive product, and the total weight of the fuel additive product is 100% by weight, or a combination thereof.

* * * * *